United States Patent
Sano et al.

(10) Patent No.: US 9,642,548 B2
(45) Date of Patent: May 9, 2017

(54) ELECTRODE PAD FOR USE ON LIVING ORGANISM

(75) Inventors: Yoshihiko Sano, Osaka (JP); Masahide Harada, Sapporo (JP)

(73) Assignees: NIPRO CORPORATION, Osaka (JP); HARADA ELECTRONICS CO., LTD., Hokkaido (JP)

( * ) Notice: Subject to any disclaimer, the term of this patent is extended or adjusted under 35 U.S.C. 154(b) by 260 days.

(21) Appl. No.: 14/404,370

(22) PCT Filed: May 28, 2012

(86) PCT No.: PCT/JP2012/063622
§ 371 (c)(1),
(2), (4) Date: Nov. 26, 2014

(87) PCT Pub. No.: WO2013/179368
PCT Pub. Date: Dec. 5, 2013

(65) Prior Publication Data
US 2015/0112176 A1    Apr. 23, 2015

(51) Int. Cl.
*A61B 5/0408*    (2006.01)
*A61B 5/0416*    (2006.01)
*A61B 5/00*    (2006.01)

(52) U.S. Cl.
CPC ........ *A61B 5/04087* (2013.01); *A61B 5/0408* (2013.01); *A61B 5/7207* (2013.01)

(58) Field of Classification Search
CPC .............. A61B 5/04087; A61B 5/0408; A61B 5/04082; A61B 5/0416; A61B 5/0492; A61B 5/0496

(Continued)

(56) References Cited

U.S. PATENT DOCUMENTS 3,993,049 A * 11/1976 Kater ................. A61B 5/04087
600/391
4,066,078 A * 1/1978 Berg .................. A61B 5/04087
600/391

(Continued)

FOREIGN PATENT DOCUMENTS

EP          0778046 A2    6/1997
JP          62-159639 A    7/1987

(Continued)

OTHER PUBLICATIONS

English translation and Japanese PCT International Search Report mailed Aug. 21, 2012, which was issued in a related PCT International Application No. PCT/JP2012/063622 (5 pages).

(Continued)

*Primary Examiner* — Lee S Cohen
(74) *Attorney, Agent, or Firm* — Robert P. Michal, Esq.; Carter, DeLuca, Farrell & Schmidt, LLP

(57) ABSTRACT

An electrode pad for use on a living organism can measure an electrocardiographic signal without being hindered by body-motion noise. The electrode pad is attached to the skin of the living organism, detects an electrical signal, and supplies the electrical signal to an electrocardiograph. The electrode pad for use on a living organism is characterized by the provision of a mesh-like electrode that extends along the skin, a conductive gel sheet that is layered on top of the electrode and extends along the surface of the skin, and a soft protective sheet that covers the layered electrode and conductive gel sheet.

1 Claim, 4 Drawing Sheets

(58) Field of Classification Search
USPC .................................................. 600/391–393
See application file for complete search history.

(56) References Cited

U.S. PATENT DOCUMENTS

| | | | | |
|---|---|---|---|---|
| 4,239,046 A * | 12/1980 | Ong | .................... | A61B 5/04087 128/DIG. 15 |
| 4,362,165 A * | 12/1982 | Carmon | ............... | A61B 5/0408 600/396 |
| 4,580,339 A * | 4/1986 | Ioffe | .................... | A61N 1/0456 29/825 |
| 4,736,752 A * | 4/1988 | Munck | ................. | A61N 1/0452 607/149 |
| 4,832,036 A * | 5/1989 | Cartmell | ............ | A61B 5/04087 600/384 |
| 5,042,144 A * | 8/1991 | Shimada | ........... | A61B 5/04087 156/235 |
| 5,263,481 A * | 11/1993 | Axelgaard | ......... | A61B 5/04085 600/384 |
| 5,366,497 A * | 11/1994 | Ilvento | ................. | A61B 5/0408 600/391 |
| 5,785,040 A | 7/1998 | Axelgaard | | |
| 6,643,532 B2 * | 11/2003 | Axelgaard | ........... | A61B 5/0416 600/391 |
| 7,697,998 B2 * | 4/2010 | Axelgaard | ........... | A61N 1/0452 607/142 |
| 2004/0225343 A1 | 11/2004 | Koike | | |

FOREIGN PATENT DOCUMENTS

| | | |
|---|---|---|
| JP | 9-131328 A | 5/1997 |
| JP | 2546264 Y2 | 5/1997 |
| JP | H09206384 A | 8/1997 |
| JP | 2004-329478 A | 11/2004 |
| JP | 2006-231020 A | 9/2006 |

OTHER PUBLICATIONS

Extended European Search Report from European Appl. No. 12878163.2 dated Dec. 18, 2015 (7 pages).

* cited by examiner

ELECTRODE PAD FOR USE ON LIVING ORGANISM

CROSS REFERENCE TO RELATED APPLICATION

This application is a U.S. National Phase Application under 35 USC 371 of International Application No. PCT/JP2012/063622 filed May 28, 2012, the entire disclosure of which is incorporated herein by reference.

TECHNICAL FIELD

The present invention relates to an electrode pad for use on a living organism that is attached to the skin of the living organism and detects an electrical signal, and supplies the electrical signal to an electrocardiograph, and especially relates to the electrode pad that can stably measure the electrocardiographic signal without being interrupted by a body-motion noise.

BACKGROUND INFORMATION

As an electrode pad for use on a living organism of the prior art, e.g. the electrode pad disclosed in the Japanese patent application laid-open No. 2006-231020 is known, which was formerly proposed by the applicant of the present application. The electrode pad for use on a living organism has a plurality of electrodes having mutually different area, each contacts a surface of a skin at a predetermined position of a living organism through conductive gel. In contact of the plurality of electrode pads with the surface of the skin on the living organism, the electrocardiograph determines a basic electrocardiographic signal by evaluating a difference of the signals from either one electrode of each of the electrode pads, while determining a body-motion noise signal by evaluating a difference of the signals from a relatively narrower electrode and a relatively wider electrode of each of the electrode pads, then enables to determine the electrocardiographic signal without being interrupted by a body-motion noise, by eliminating the low-frequency component of the body-motion noise signal from the basic electrocardiographic signal. Incidentally, the body-motion noise signal is assumed to be generated due to fluctuating of polarization potential or impedance between an electrode and conductive gel or between conductive gel and a surface of the skin.

PRIOR ART DOCUMENT

Patent Related Document

Document 1: Japanese patent application laid-open No. 2006-231

SUMMARY

Problem to be Solved by the Invention

Along with advance of the investigation by the inventors in regard to the electrode pad for use on a living organism of the prior art, following problem is newly discovered. That is, with the electrode pad for use on a living organism of the prior art, because the electrocardiographic signal is detected by a hard electrode which do not follow the movement of a surface of the skin, the electrode partially separates from or comes close to the surface of the skin when body-motion occurs, which causes great fluctuations of polarization potential or impedance. Therefore, it is proved that the electrode pad for use on a living organism of the prior art still admits of improvement for measuring of electrocardiographic signal without being interrupted by a body-motion noise.

Means to Solve the Problems

The present invention solves the problem of the electrode pad for use on a living organism of the prior art advantageously by reference to the point above. The electrode pad for use on a living organism in accordance with the present invention is attached to a skin of the living organism and detects an electrical signal, and supplies the electrical signal to an electrocardiograph, characterized in that the electrode pad for use on a living organism comprises a mesh-like electrode extending along a surface of the skin, a conductive gel sheet layered to the electrode and extending along the surface of the skin, and a soft protective sheet covering the electrode and the conductive gel sheet in the mutually layered condition.

Effect of the Invention

In the electrode pad for use on a living organism, when the electrode pad for use on a living organism is attached on the surface of the skin at a predetermined position of a living organism, the mesh-like electrode extends along the surface of the skin with a sufficient area and contacts the surface of the skin through the conductive gel sheet or directly, and detects and outputs an electric signal while deforming, expanding or contracting by flexibly following the motion of the surface of the skin. The conductive gel sheet layered to the mesh-like electrode also extends along the surface of the skin with a sufficient area and contacts the surface of the skin at substantially the same position of the living organism as the electrode placing, contacting the electrode with sufficient area while contacting the surface of the skin with sufficient area due to the conductive gel of the conductive gel sheet permeating through the mesh of the electrode and contacting the electrode with sufficient area by contacting many parts of a surface of the conductive material forming the mesh, then detects and transmits an electric signal to the electrode while deforming, expanding or contracting by flexibly following the motion of the surface of the skin. Further, the soft protective sheet protects the electrode and the conductive gel sheet by covering the electrode and the conductive gel sheet while permitting the electrode and the conductive gel sheet deforming, expanding or contracting by flexibly following the motion of the surface of the skin.

Therefore, with the electrode pad for use on a living organism in accordance with the present invention, because the electrode and the conductive gel sheet contact the surface of the skin with sufficient area and mutually contact with sufficient area, a sufficient level of electrocardiographic signal can be detected by the electrode. In addition, because the electrode and the conductive gel sheet detect the electrocardiographic signal while deforming, expanding or contracting by flexibly following the motion of the surface of the skin, even if movement of the surface of the skin occurs due to a body-motion, substantial fluctuating of polarization potential or impedance does not occur, so that body-motion noise signal level is suppressed, thus the electrocardiographic signal can be measured without being interrupted by a body-motion noise.

Incidentally, in the electrode pad for use on a living organism in accordance with the present invention, it is preferable that the electrode is positioned between the conductive gel sheet and the protective sheet. With this constitution, because the mesh-like electrode is sandwiched between the conductive gel sheet and the protective sheet and protected by the sheets, the mesh-like electrode can be prevented from being raveled out or involuntarily deformed during using of the present electrode pad for use on a living organism.

In the case above, in the electrode pad for use on a living organism in accordance with the present invention, it is preferable that the protective sheet extends over a peripheral edge of the electrode and adheres to the conductive gel sheet with adhesive on a back surface thereof. With this constitution, because whole of the mesh-like electrode is enveloped by the protective sheet and the conductive gel sheet, the mesh-like electrode can be protected more reliably.

On the other hand, in the electrode pad for use on a living organism in accordance with the present invention, it is preferable that the conductive gel sheet is positioned between the electrode and the protective sheet. With this constitution, because the mesh-like electrode directly contacts the surface of the skin, the electrocardiographic signal can be measured at higher level.

EMBODIMENTS OF THE INVENTION

Figure 1:
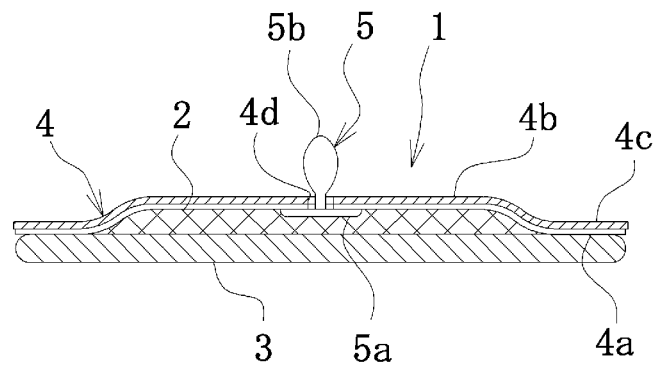
FIG. 1 (*a*) is a sectional view showing the first example of the electrode pad for use on a living organism in accordance with the present invention, FIG. 1 (*b*) is a perspective view schematically showing an electrode of the electrode pad of the example, and FIG. 1 (*c*) is a sectional view showing the electrode pad of the example in a condition that the electrode pad is attached on a surface of a skin.
Figure 1:
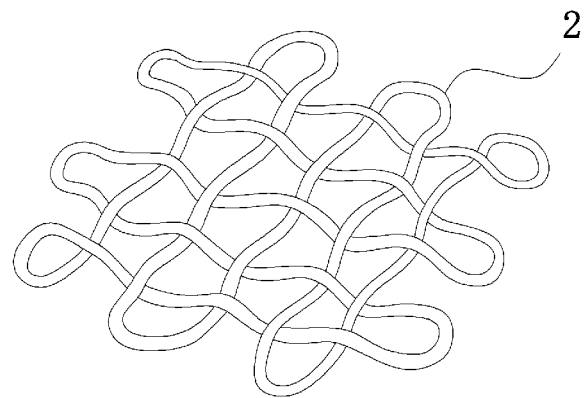
Figure 1:
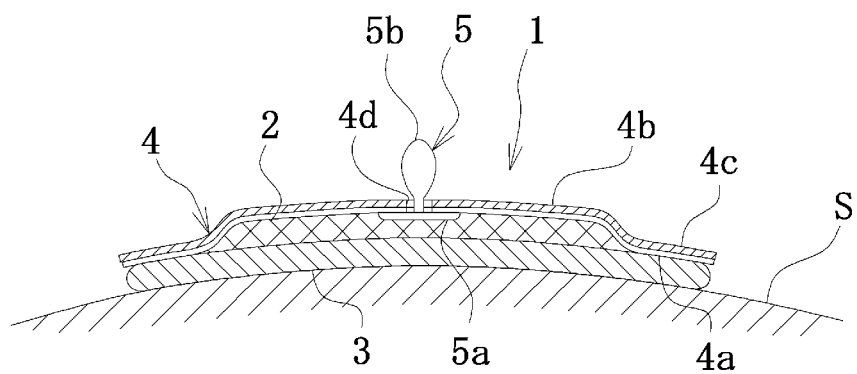

Embodiments of the present invention will be explained in detail with examples below, referring to drawings attached herewith. FIG. 1 (*a*) is a sectional view showing the first example of the electrode pad for use on a living organism in accordance with the present invention, FIG. 1 (*b*) is a perspective view schematically showing an electrode of the electrode pad of the example, and FIG. 1 (*c*) is a sectional view showing the electrode pad of the example in a condition that the electrode pad is attached on a surface of a skin. In the drawings, the reference numeral 1 indicates the electrode pad of the first example.

The electrode pad 1 of the example is the one that is attached to a skin of a living organism and detects an electrical signal, and supplies the electrical signal to an electrocardiograph, and comprises, as shown in FIG. 1 (*a*), an electrode 2, a conductive gel sheet 3 layered below the electrode 2 in the drawings, a soft protective sheet 4 covering the electrode 2 and the conductive gel sheet 3 from above in the drawings, and a connecting terminal 5 electrically connected to the electrode 2. Wherein, the electrode 2 forms a generally flat and circular mesh-like structure as a whole by braiding a metallic wire such as a copper wire as a conductive material, as shown in FIG. 1 (*b*), and positioned between the conductive gel sheet 3 and the protective sheet 4. Incidentally, though the metallic wire exposes the metallic surface and forms a loop-like structure by connecting the both ends to prevent raveling out of the mesh in the example shown in the drawings, both ends of the metallic wire can be mutually disconnected. Further, the conductive gel sheet 3 is a regular one that is made by permeating an adhesive conductive gel to a circular e.g. fabric-like base body larger than the electrode 2, and as explained below, adheres the peripheral portion on an outer peripheral end of a back surface of the protective sheet 4 so as to envelope and fix a whole of the electrode 2 between the protective sheet 4 and the conductive gel sheet 3 while permeating the conductive gel through the mesh of the electrode 2 and adhering to the intermediate portion of the back surface of the protective sheet 4.

The protective sheet 4 is mainly formed from an e.g. circular soft nonconductive material such as a plastic film and so on, and has a felt layer 4*a* adhered on a whole of a back surface (the lower surface in the drawings) of the nonconductive material. The protective sheet has an intermediate portion 4*b* and an outer peripheral portion 4*c*. The intermediate portion 4*b* covers the electrode 2 and the conductive gel sheet 3 from above in the drawings and holds the electrode 2 and the conductive gel sheet 3 in the mutually layered condition by adhering of the felt layer 4*a* and conductive gel of the conductive gel sheet 3 permeating through the mesh of the electrode 2. The outer peripheral portion 4*c* continuing from the intermediate portion 4*b* and positioned outward of the electrode 2 in the elongating direction of the electrode 2 (right and left directions in the drawings) holds the outer peripheral portion of the conductive gel sheet 3 which positions outward of the periphery of the electrode 2 by adhering of the felt layer 4*a* and the conductive gel of the conductive gel sheet 3, so as to protect a whole of the mesh-like electrode 2 by enveloping between the protective sheet 4 and the conductive gel sheet 3.

The connecting terminal 5 has a small disk-like base portion 5*a* sandwiched between the central portion of the mesh-like electrode 2 and the intermediate portion 4*b* of the protective sheet 4 and electrically connected to the electrode 2 e.g. directly or by soldering and so on, and a spindle-like connecting portion 5*b* projecting from the base portion 5*a* to the outside of the protecting sheet 4 through a penetrating hole 4*d* of the intermediate portion 4*b* of the protective sheet 4. The base portion 5*a* and the connecting portion 5*b* are formed integrally from a base material of e.g. plastic as a whole, and an outer surface thereof are covered by e.g. silver plating or silver chloride plating or silver chloride coating as a good conductive metal.

Further, in the electrode pad 1 of the example for use on a living organism, there is provided a peelable sheet which is not shown in the drawings, made from a regular film surface-treated to be easily peeled from the conductive gel sheet 4 so that the peelable sheet covers a whole of the conductive gel sheet 4 to protect the sheet 4 during nonuse time period of the electrode pad 1.

In the electrode pad 1 of the example for use on a living organism, when the peelable sheet is peeled from the conductive gel sheet 4 and then, as shown in FIG. 1 (c), the electrode pad 1 for use on a living organism is attached on the surface S of the skin at a predetermined position of a living organism and the connecting portion 5b of the connecting terminal 5 is connected to an electrocardiograph which is not shown in the drawings, the mesh-like electrode 2 of the electrode pad 1 extends along the surface S of the skin with a sufficient area and contacts the surface S of the skin through the conductive gel sheet 3, and detects and outputs an electric signal from the surface S while deforming, expanding or contracting by flexibly following the motion of the surface S of the skin. The conductive gel sheet 3 layered to the mesh-like electrode 2 also extends along the surface S of the skin with a sufficient area and contacts the surface S of the skin at substantially the same position of the living organism as the electrode 2 placing, contacting the electrode 2 with sufficient area while contacting the surface S of the skin with sufficient area due to the conductive gel of the conductive gel sheet 3 permeating through the mesh of the electrode 2 and contacting the electrode 2 with sufficient area by contacting many parts of a surface of the metallic wire forming the mesh, then detects and transmits an electric signal to the electrode 2 while deforming, expanding or contracting by flexibly following the motion of the surface S of the skin. Further, the soft protective sheet 4 protects the electrode 2 and the conductive gel sheet 3 by covering the electrode 2 and the conductive gel sheet 3 while permitting the electrode 2 and the conductive gel sheet 3 deforming, expanding or contracting by flexibly following the motion of the surface S of the skin.

Therefore, with the electrode pad 1 of the example for use on a living organism, because the electrode 2 and the conductive gel sheet 3 contact the surface S of the skin with sufficient area and mutually contact with sufficient area, a sufficient level of electrocardiographic signal can be detected by the electrode 2 and supplied from the connecting terminal 5 to the electrocardiograph. In addition, because the electrode 2 and the conductive gel sheet 3 detect the electrocardiographic signal while deforming, expanding or contracting by flexibly following the motion of the surface S of the skin, even if movement of the surface S of the skin occurs due to a body-motion, substantial fluctuating of polarization potential or impedance does not occur, so that body-motion noise signal level is suppressed, thus the electrocardiographic signal can be measured without being interrupted by a body-motion noise.

Further, with the electrode pad 1 of the example for use on a living organism, the electrode 2 is positioned between the conductive gel sheet 3 and the protective sheet 4. Therefore, because the mesh-like electrode 2 is sandwiched between the conductive gel sheet 3 and the protective sheet 4 so that the electrode 2 is protected by the sheets 3 and 4, the mesh-like electrode 2 can be prevented from being raveled out or involuntarily deformed during using of the present electrode pad 1 for use on a living organism.

Further with the electrode pad 1 of the example for use on a living organism, the protective sheet 4 extends over the peripheral edge of the electrode 2 and adheres to the conductive gel sheet 3 with felt layer 4a on the back surface thereof. Therefore, because whole of the mesh-like electrode 2 is enveloped by the protective sheet 4 and the conductive gel sheet 3, the mesh-like electrode 2 can be protected more reliably.

Figure 2:
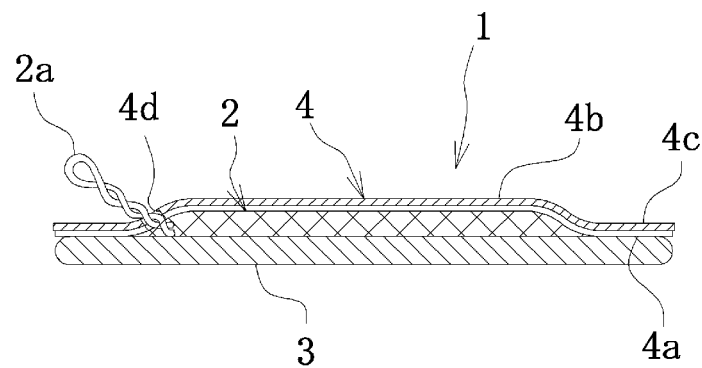
FIG. 2 (*a*) is a sectional view showing the second example of the electrode pad for use on a living organism in accordance with the present invention, FIG. 2 (*b*) is a perspective view schematically showing an electrode of the electrode pad of the example, and FIG. 2 (*c*) is a sectional view showing the electrode pad of the example in a condition that the electrode pad is attached on a surface of a skin.
Figure 2:
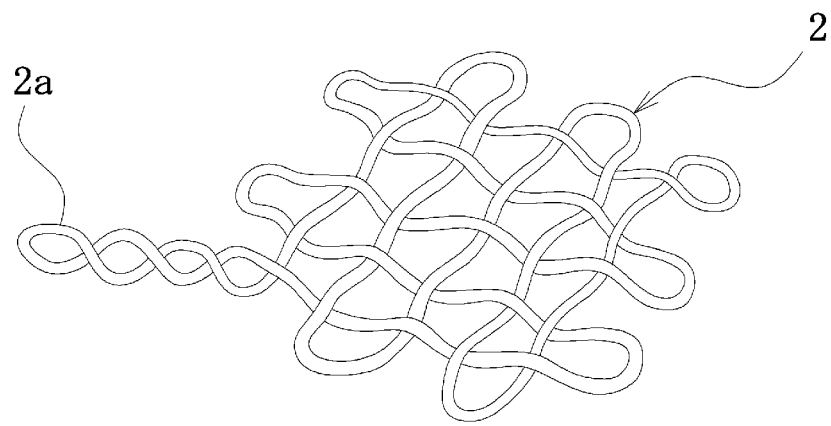
Figure 2:
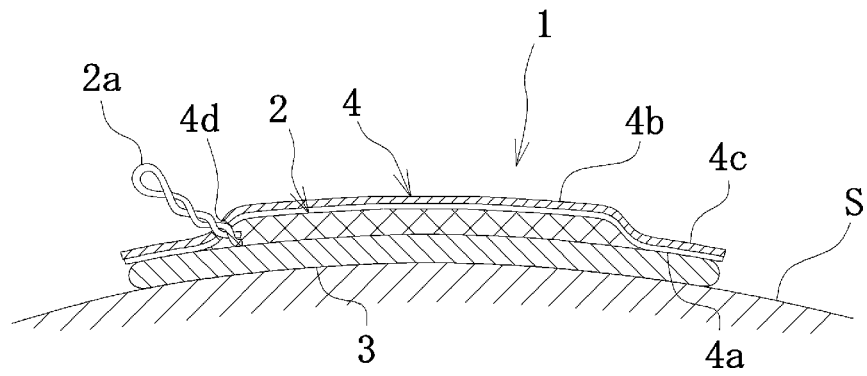

FIG. 2 (a) is a sectional view showing the second example of the electrode pad for use on a living organism in accordance with the present invention, FIG. 2 (b) is a perspective view schematically showing an electrode of the electrode pad of the example, and FIG. 2 (c) is a sectional view showing the electrode pad of the example in a condition that the electrode pad is attached on a surface of a skin. In the drawings, a part similar to that in the former example is indicated by the same reference numeral.

The electrode pad 1 of the example for use on a living organism is different from the former example only in the point that, instead of the connecting terminal 5 of the former example, as shown in FIG. 2(b), connecting portion 2a is formed by elongating a part of the metallic wire forming the electrode 2 from the other part thereof, then the connecting portion 2a formed from the metallic wire is projected to the outside of the protecting sheet 4 through a penetrating hole 4d of the intermediate portion 4b of the protective sheet 4. Other points of the example are constituted similarly to the former example.

With the electrode pad 1 of the example for use on a living organism, action and effect similar to that of the former example can be attained. Further, especially with the electrode pad 1 of the example for use on a living organism, instead of providing the hard connecting terminal 5 formed from the base material made of e.g. plastic, the connecting portion 2a for connecting to an electrocardiograph is formed by elongating a part of the metallic wire forming the electrode 2 from the other part thereof. Therefore, as shown in FIG. 2 (c), the electrode 2 can deform, expand or contract more flexibly following the motion of the surface S of the skin, so that body-motion noise signal level is more suppressed, thus detecting level of the electrocardiographic signal can be developed to a higher level, while the electrode pad 1 for use on a living organism can be produced with lower cost.

Figure 3:
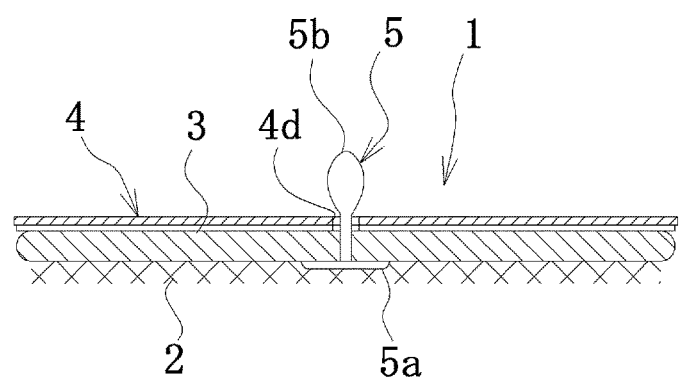
FIG. 3 (*a*) is a sectional view showing the third example of the electrode pad for use on a living organism in accordance with the present invention, and FIG. 3 (*b*) is a sectional view showing the electrode pad of the example in a condition that the electrode pad is attached on a surface of a skin.
Figure 3:
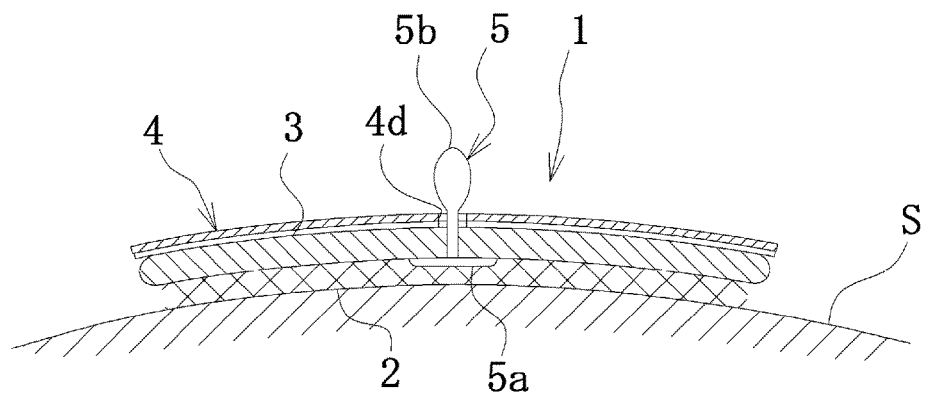

FIG. 3 (a) is a sectional view showing the third example of the electrode pad for use on a living organism in accordance with the present invention, and FIG. 3 (b) is a sectional view showing the electrode pad of the example in a condition that the electrode pad is attached on a surface of a skin. In the drawings, a part similar to that in the former example is indicated by the same reference numeral.

The electrode pad 1 of the example for use on a living organism is different from the former first example in the point that the order of layering of the electrode 2 and the conductive gel sheet 3. That is, as shown in FIG. 3 (a), the conductive gel sheet 3 is positioned between the electrode 2 and the protective sheet 4. Further, the electrode 2 has almost same size as the conductive gel sheet 3 and the protective sheet 4. Then, in the electrode pad 1 of the example for use on a living organism, the small disk-like base portion 5a of the connecting terminal 5 is positioned between the central portion of the mesh-like electrode 2 and the conductive gel sheet 3 and electrically connected to the electrode 2 by e.g. directly connecting or soldering and so on, and a spindle-like connecting portion 5b projecting from the base portion 5a penetrates the conductive gel sheet 3 and projects to the outside of the protecting sheet 4 through a penetrating hole 4d of the intermediate portion 4b of the protective sheet 4. Other points of the example are constituted similarly to the former first example.

With the electrode pad 1 of the example for use on a living organism, action and effect similar to that of the first example can be attained. Further, especially with the electrode pad 1 of the example for use on a living organism, as shown in FIG. 3 (b), the mesh-like electrode 2 directly contacts on the surface S of the skin, so that detecting level of the electrocardiographic signal can be developed to a higher level.

Figure 4:
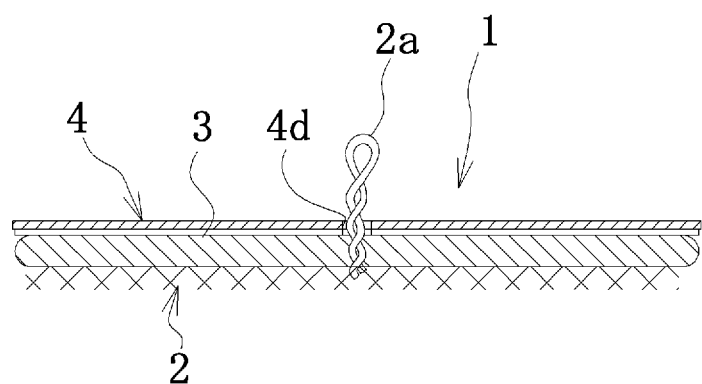
FIG. 4 (*a*) is a sectional view showing the fourth example of the electrode pad for use on a living organism in accordance with the present invention, and FIG. 4 (*b*) is a sectional view showing the electrode pad of the example in a condition that the electrode pad is attached on a surface of a skin.
Figure 4:
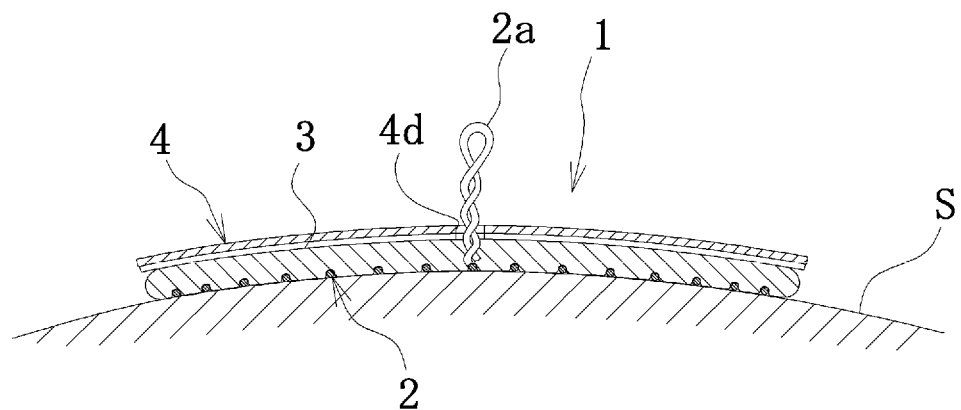

FIG. 4 (a) is a sectional view showing the fourth example of the electrode pad for use on a living organism in accordance with the present invention, and FIG. 4 (b) is a sectional view showing the electrode pad of the example in a condition that the electrode pad is attached on a surface of a skin. In the drawings, a part similar to that in the former example is indicated by the same reference numeral.

The electrode pad 1 of the example for use on a living organism is different from the former second example in the point that the order of layering of the electrode 2 and the conductive gel sheet 3. That is, as shown in FIG. 4 (a), the conductive gel sheet 3 is positioned between the electrode 2 and the protective sheet 4. Further, the electrode 2 has almost the same size as the conductive gel sheet 3 and the protective sheet 4. Then, in the electrode pad 1 of the example for use on a living organism, the connecting portion 2a formed from the metallic wire of the electrode 2 penetrates the conductive gel sheet 3 and projects outside through a penetrating hole 4d of the central portion of the protective sheet 4. Other points of the example are constituted similarly to the former example.

With the electrode pad 1 of the example for use on a living organism, action and effect similar to that of the second example can be attained. Further, especially with the electrode pad 1 of the example for use on a living organism, as shown in FIG. 4 (b), the mesh-like electrode 2 directly contacts on the surface S of the skin, so that detecting level of the electrocardiographic signal can be developed to a higher level. In addition, instead of providing the connecting terminal 5, the connecting portion 2a for connecting to an electrocardiograph is formed by elongating a part of the metallic wire forming the electrode 2 from the other part thereof, so that the electrode pad 1 for use on a living organism can be produced with lower cost.

Though the embodiments are explained above based on the examples shown in the drawings, the present invention is not limited by the examples above, the present invention can be changed appropriately in the scope of the description recited in the claims. That is, e.g. though in the example the metallic wire forming the electrode 2 exposes the metallic surface, the surface of the metallic wire forming the electrode 2 may be covered by e.g. silver plating or silver chloride plating or silver chloride coating as a good conductive metal. Further, though in the example the mesh-like electrode is formed by braiding a metallic wire, the electrode 2 may be formed in the mesh-like grid structure from a metal plate and so on by punching with pressing or etching and so on.

INDUSTRIAL APPLICABILITY

Thus, with the electrode pad for use on a living organism in accordance with the present invention, because the electrode and the conductive gel sheet contact the surface of the skin with sufficient area and mutually contact with sufficient area, a sufficient level of electrocardiographic signal can be detected by the electrode. In addition, because the electrode and the conductive gel sheet detect the electrocardiographic signal while deforming, expanding or contracting by flexibly following the motion of the surface of the skin, even if movement of the surface of the skin occurs due to a body-motion, substantial fluctuating of polarization potential or impedance does not occur, so that body-motion noise signal level is suppressed, and the electrocardiographic signal can be measured without being interrupted by a body-motion noise.

EXPLANATION OF REFERENCE NUMERALS 1. electrode pad for use on a living organism
2. electrode
2a. connecting portion
3. conductive gel sheet
4. protective sheet
4a. felt layer
4b. intermediate portion
4c. outer peripheral portion
4d. penetrating hole
5. connecting terminal
5a. base portion
5b. connecting portion
S. surface of skin

The invention claimed is:

1. An electrode pad for use on a living organism, which is adapted to attach to skin of the living organism and detects an electrical signal, and supplies the electrical signal to an electrocardiograph, the electrode pad comprising:
   a mesh-like electrode adapted to extend along a surface of the skin;
   a conductive gel sheet layered to the mesh-like electrode and adapted to extend along the surface of the skin; and
   a soft protective sheet covering the mesh-like electrode and the conductive gel sheet in the mutually layered condition,
   wherein the conductive gel sheet is positioned between the mesh-like electrode and the protective sheet, while the mesh-like electrode has an area equal to the conductive gel sheet and the mesh-like electrode is layered outside of the conductive gel sheet so that the mesh-like electrode is adapted to contact the surface of the skin.

* * * * *